United States Patent
Nakashima et al.

(10) Patent No.: US 7,235,621 B2
(45) Date of Patent: Jun. 26, 2007

(54) PROCESS FOR PRODUCING COPOLYESTER

(75) Inventors: Toshimitsu Nakashima, Takasago (JP);
Osamu Odawara, Takasago (JP);
Satoru Yokomizo, Akashi (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 10/528,781

(22) PCT Filed: Oct. 10, 2003

(86) PCT No.: PCT/JP03/13021

§ 371 (c)(1),
(2), (4) Date: Nov. 28, 2005

(87) PCT Pub. No.: WO2004/033701

PCT Pub. Date: Apr. 22, 2004

(65) Prior Publication Data

US 2006/0128934 A1    Jun. 15, 2006

(30) Foreign Application Priority Data

Oct. 10, 2002    (JP) .............................. 2002-297602

(51) Int. Cl.
*C08G 63/02*    (2006.01)

(52) U.S. Cl. ...................... 528/272; 435/69.1; 435/232; 435/252.3; 435/320.1; 525/444; 525/450; 528/271; 536/23.2; 536/23.7

(58) Field of Classification Search ............... 435/69.1, 435/232, 252.3, 320.1; 525/444, 450; 536/23.2, 536/23.7
See application file for complete search history.

(56) References Cited

U.S. PATENT DOCUMENTS 4,393,167 A    7/1983    Holmes et al.
4,997,909 A    3/1991    Doi
5,981,257 A    11/1999   Fukui et al.

FOREIGN PATENT DOCUMENTS

| EP | 0 114 086 A2 | 7/1984 |
|---|---|---|
| EP | 0 204 442 A2 | 12/1988 |
| EP | 0 533 144 A2 | 3/1993 |
| EP | 0 824 148 A2 | 2/1998 |
| JP | 57-150393 | 9/1982 |
| JP | 59-220192 | 12/1984 |
| JP | 63-269989 | 11/1988 |
| JP | 5-93049 | 4/1993 |
| JP | 7-79705 | 8/1995 |
| JP | 7-265065 | 10/1995 |
| JP | 10-108682 | 4/1998 |
| JP | 11-500008 | 1/1999 |
| JP | 2001-340078 | 12/2001 |
| WO | WO 96/25509 | 8/1996 |

OTHER PUBLICATIONS

Lee, Seung Hwan, et al. "Production of Poly(3-Hydroxybutyrate-co-3-Hydroxyhexanoate) by High-Cell-Density Cultivation of *Aeromonas hydrophila*," Biotechnology and Bioengineering, vol. 67, No. 2, Jan. 20, 2000, pp. 240-244.

Chen, G. Q., et al., "Industrial scale production of poly (3-hydroxybutyrate-co-3-hydroxhexanoate)," *Appl. Microbiol. Biotechnol.*, vol. 57, No. 1/2, 2001, pp. 50-55.

Zhang, Jin, et al., "Production of Poly(3-Hydroxybutyrate-co-3-Hydroxyhexanoate) by *Aeromonas hydrophila* 4AK4 Grown on Soybean", *Journal of Food Science and Biotechnology*, vol. 21 No. 1, Jan. 2002, pp. 76-79.

*Primary Examiner*—Terressa Boykin
(74) *Attorney, Agent, or Firm*—Kenyon & Kenyon LLP

(57) ABSTRACT

Process for producing a copolyester of desired quality at low cost with high productivity, preferably a process for producing P(3HB-co-3HH) of 4 mol % or more 3HH content with a productivity as high as 40 g/L or more. In particular, a process for producing a copolyester of 3HB and 3HH comprising culturing a microorganism with the use of, as a carbon source, a fat or oil containing lauric acid as a constituent fatty acid under such conditions that phosphorus as a source of nutrition is limited.

6 Claims, 1 Drawing Sheet

PROCESS FOR PRODUCING COPOLYESTER

This is a 371 national phase application of PCT/JP2003/013021 filed 10 Oct. 2003, claiming priority to Japanese Application No. 2002-297602 filed 10 Oct. 2002, the contents of which are incorporated herein by reference.

TECHNICAL FIELD

The present invention relates to a method for producing a copolyester comprising 3-hydroxybutyric acid (hereinafter, referred to briefly as "3HB") and 3-hydroxyhexanoic acid (hereinafter, referred to briefly as "3HH") as monomeric units by using a microorganism.

BACKGROUND ART

Up to now, a large number of microorganisms have been known to store polyester as an energy source substance within cells. A typical example of the polyester is poly-3-hydroxybutyric acid (hereinafter referred to briefly as "P(3HB)"). P(3HB) is a thermoplastic polymer and is biodegradable in the natural environment and, thus, has recently attracted attention as an ecofriendly green plastic. However, since P(3HB) is high in crystallinity, it is hard and fragile, so that the range of practical application thereof is limited. Therefore, studies have been undertaken to modify the P(3HB) for improving these properties.

In the course of the study, a copolymer P(3HB-co-3HV) derived from 3-hydroxybutyric acid (3HB) and 3-hydroxyvaleric acid (hereinafter referred to briefly as "3HV"), and a production method thereof have been developed (Japanese Kokai Publication Sho-57-150393, Japanese Kokai Publication Sho-59-220192 and Japanese Kohyo Publication Hei-11-500008). This P(3HB-co-3HV) is rich in flexibility as compared with P(3HB), hence it was considered to have a wide application range.

Methods for producing the copolymer P(3HB-co-3HV) described in these patent documents comprise growing cells in the first stage and culturing a microorganism with restricting nitrogen or phosphorus in the latter stage to produce the copolymer similarly to the conventional methods for producing P(3HB).

Moreover, as for P(3HB-co-3HV), since the flexibility changes as a content of 3HV increases, researches for controlling the 3HV content have also been made. For example, propionic acid is used in Japanese Kokai Publication Sho-57-150393 and Japanese Kokai Publication Sho-63-269989, and propan-1-ol is used in Japanese Kokoku Publication Hei-7-79705, and by changing an addition amount thereof to a medium, the 3HV content in P(3HB-co-3HV) is controlled to produce P(3HB-co-3HV) having the 3HV content of 10 to 90 mol %.

Actually, however, P(3HB-co-3HV) shows only slight changes in the characteristics even when the 3HV content is increased. In particular, the flexibility is not improved to such an extent required for its use in films and the like. Thus, it has been used only in the field of rigid shaped articles such as shampoo bottles and disposable razor grips.

Under such circumstances, for making up the above-mentioned drawbacks of the copolymer derived from 3HB and 3HV, copolymers containing, as a component, a hydroxyalkanoic acid other than 3HB and 3HV such as 3-hydroxypropionic acid (hereinafter referred to briefly as "3HP"), 3-hydroxyhexanoic acid (hereinafter referred to briefly as "3HH"), 3-hydroxyoctanoic acid (hereinafter referred to briefly as "3HO"), 3-hydroxynonanoic acid (hereinafter referred to briefly as "3HN"), 3-hydroxydecanoic acid (hereinafter referred to briefly as "3HD") or 3-hydroxydodecanoic acid (hereinafter referred to briefly as "3HDD") are intensively studied (Poirier, Y., Nawrath C., Somerville C, BIO/TECHNOLOGY, 13, 142–150, 1995).

Among them, noteworthy studies are those on a copolyester comprising 3HB and 3HH units, particularly a copolymer P(3HB-co-3HH) derived only from 3HB and 3HH, and on a production method thereof (Japanese Kokai Publication Hei-05-93049 and Japanese Kokai Publication Hei-07-265065). The production methods of copolyesters such as P(3HB-co-3HH) described in these patent documents comprise a fermentation production from fatty acids such as oleic acid or oils and fats such as olive oil by using *Aeromonas caviae* isolated from soil.

A study regarding characteristics of P (3HB-co-3HH) has also been conducted (Y. Doi, S. Kitamura, H. Abe, Macromolecules 28, 4822–4823, 1995). This document reports a fermentation production of P (3HB-co-3HH) with a 3HH content of 11 to 19 mol % by culturing *A. caviae* with a fatty acid of not less than 12 carbon atoms. The result shows that, as the 3HH content increases, P(3HB-co-3HH) exhibits a gradual increase of flexibility from the hard and brittle characteristics of P (3HB) and finally shows more flexibility than P(3HB-co-3HV).

Additionally, it was reported that a polyhydroxyalkanoic acid(PHA) synthase gene from *A. caviae* was cloned and introduced into *R. eutropha* having an accumulating ability of polyhydroxybutyric acid(PHB) of not less than 90% to generate a recombinant strain, which was then used to produce P (3HB-co-3HH) using fatty acids as a carbon source (T. Fukui, Y. Doi, J. Bacteriol., vol. 179, No. 15, 4821–4830, 1997 and Japanese Kokai Publication Hei-10-108682). In these documents, it is reported that P (3HB-co-3HH) having the 3HH content of 10 to 20 mol % may be produced by using sodium octanoate as a carbon source.

Furthermore, a method has been recently disclosed which comprises using multiple carbon sources in producing a polyester using the above recombinant strain, and it was revealed that a carbon number of an oil or fat or a fatty acid used as a carbon source had an influence on the 3HH-content of P(3HB-co-3HH) (Japanese Kokai Publication 2001-340078).

If the 3HH content of P(3HB-co-3HH) can be controlled optionally in a wide range in the future, both hard copolymers and soft copolymers may be produced by fermentation, and such copolymers will find a broad range of applications, from chassis for TV-set, which is required to be hard, to a thread or a film, which are required to be flexible.

However, when a practical application of P(3HB-co-3HH) is considered, what becomes a barrier is the production cost. For example, in any methods which have already been disclosed, the productivity of P(3HB-co-3HH) is low and it is as much as 30 g/L. Additionally, a fatty acid having the carbon number of not less than 12, which is expensive as a carbon source, is used as the only carbon source, or an addition of an expensive fatty acid (hexanoic acid) is required to improve the 3HH content. Thus, it is scarcely possible to apply such technologies to an industrial production method of said polymer.

As described above, characteristics of P(3HB-co-3HH) are remarkably affected by the 3HH content. As a result of the investigation conducted by the present inventors, it is preferable to secure not less than 4 mol % of the 3HH content in order to enable wide applications of P(3HB-co-3HH). However, in the conventional culture methods, not only an expensive carbon source is required but also the productivity tends to be more deteriorated when trying to improve the 3HH content (see Japanese Kokai Publication 2001-340078).

Whereupon, it has been long awaited to develop a technology for realizing a high productivity of cells and polymer content in low cost, and from an industrial point of view, a technology capable of producing P(3HB-co-3HH) having the higher productivity, and preferably, a technology capable of producing P(3HB-co-3HH) having not less than 4 mol % of the 3HH content while securing that productivity.

SUMMARY OF THE INVENTION

In view of the above-mentioned state of the art, the present invention provides a method for producing P(3HB-co-3HH) which realizes a high productivity in low cost, and preferably a method for producing P(3HB-co-3HH) having not less than 4 mol % of the 3HH content while securing that productivity.

The present inventors have made various investigations, and particularly have studied on various fermentation materials (carbon sources) in view of prices, supply stability, quality stability, yield of cells or polymers and the like. As a result, they have succeeded in maintaining the high productivity by culturing a microorganism accumulating P(3HB-co-3HH) in a medium with an inexpensive oil or fat as a carbon source, and further selecting the species of the oil or fat to be used as a carbon source and culturing conditions. Moreover, they have also succeeded in achieving the 3HH content of not less than 4 mol %, which is the desired value, by further restricting the content of specific oils and fats.

That is, the point of the present invention relates to a method for producing a copolyester which secures the high productivity of not less than 40 g/L by restricting phosphorus, a nutrient source and using an oil or fat containing lauric acid in constituent fatty acids as a carbon source in producing a copolyester derived from 3HB and 3HH, such as P(3HB-co-3HH), using a microorganism. Furthermore, the present invention relates to a method for producing a copolyester having the 3HH content of preferably not less than 4 mol % by further restricting the content of lauric acid in constituent fatty acids of the oil or fat to be used as a carbon source to be not less than 10% by weight.

DETAILED DESCRIPTION OF THE INVENTION

The present invention is a method for producing a copolyester comprising at least 3-hydroxybutyric acid and 3-hydroxyhexanoic acid as monomeric units which comprises culturing an oil or fat containing lauric acid in constituent fatty acids as a carbon source under a condition phosphorus, a nutrient source, being restricted.

The method for producing the copolyester according to the present invention is applied in producing a copolyester comprising 3HB and 3HH units as monomeric units such as P(3HB-co-3HH) using a microorganism.

The copolyester produced by the method of the present invention is a polyester comprising at least 3HB and 3HH as a monomeric unit, and it may also contain a monomeric unit other than 3HB and 3HH. As the third monomeric unit in this case, there may be mentioned 3HV, 3HP, 3HO, 3HN, 3HD and 3HDD, etc. However, in order to copolymerize monomeric units having odd number of carbon chains such as 3HV, it is required to add a carbon source having odd number of carbon chains, which scarcely exists in natural oils and fats available as an inexpensive carbon source in the culture method described below.

From an advantageous point of view such as a culture cost or other merits on a process, it is preferable to use P(3HB-co-3HH) derived only from 3HB and 3HH as a copolyester produced by the method according to the present invention.

When the production method of the present invention is used, the productivity of the copolyester by a microorganism becomes not less than 40 g/L. In the present specification, "the productivity of a copolyester" is represented by a weight of the produced copolyester in a volume of medium fluid (medium+microorganism+other by-product) at the time of completion of the culture.

The content of 3-hydroxyhexanoic acid in the copolyester produced by the production method of the present invention is preferably not less than 4 mol %.

It is further preferred that the productivity of the copolyester by a microorganism is not less than 40 g/L and the content of 3-hydroxyhexanoic acid in the copolyester is not less than 4 mol % in the production method of the present invention.

In the production method according to the present invention, there is no particular restriction on a microorganism to be used. For example, there may be used microorganisms isolated from nature or those deposited to deposit authorities of strains (e.g. IFO, ATCC, etc.) and bacteria of genus *Alcaligenes*, genus *Ralstonia*, genus *Aeromonas*, genus *Pseudomonas*, genus *Escherichia* and the like. Among them, preferred is *Ralstonia eutropha*.

Moreover, in the case that a wild-type of the above microorganisms cannot produce an objective copolymer, or the case that the production amount is low, the above microorganisms may be used in the form of a transformed microorganism after being transformed using a recombinant vector containing a polyester polymerase gene. As the vector used in producing the transformed microorganism, there may be used a plasmid vector and the like which is able to grow within the cell autonomously. Also, said polyester polymerase gene may be directly incorporated into the chromosome of the microorganism to be a host.

As a microorganism to be the host mentioned above, there may be used bacteria such as one belonging to the genus *Alcaligenes*, genus *Ralstonia*, genus *Aeromonas*, genus *Pseudomonas* or genus *Escherichia*.

The polyester polymerase gene to be used in the method for producing a polyester according to the present invention is not particularly restricted. However, preferred is a gene isolated from *Aeromonas caviae*, and for example, there may be used a gene fraction described in Japanese Kokai Publication Hei-10-108682 and the like.

The conventional methods may be applied in introducing the recombinant vector to the microorganism. For example, the conjugation method, the calcium method, the electroporation method and the like may be used.

As a preferable example of the microorganisms to be used in the present invention, there may be mentioned a *Ralstonia eutropha* strain PHB-4/pJRDEE32d13, which was obtained by introducing a polyester polymeraze gene derived from *Aeromonas caviae* into *Ralstonia eutropha* (T. Fukui., Y. Doi., Appl. Microbiol. Biotechnol., 49, 333–336 (1998)). This strain is deposited to the National Institute of Advanced Industrial Science and Technology, International Patent Organism Depositary (Central 6, 1-1-1, Higashi, Tsukuba, Ibaraki, JAPAN) on the date of Aug. 7, 1997 under the name of *Alcaligenes eutrophus* AC 32 in an accession number of FERM BP-6038 under Budapest treaty.

In the production of the copolyester of the present invention, an inexpensive oil or fat containing lauric acid is used as a carbon source from viewpoints of price, supply stability, quality stability, yield of cells or polymers, and the like.

A medium containing a nitrogen source, inorganic salts, vitamins and other general organic nutrient sources may be used as a nutrient source other than the carbon source.

As the nitrogen source to be used in the production method according to the present invention, there may be mentioned inorganic nitrogen sources e.g. ammonia, ammonium salts such as ammonium chloride, ammonium sulfate and ammonium phosphate, and organic nitrogen sources such as peptone, meat extract and yeast extract, for instance.

As the inorganic salts, there may be used phosphates such as potassium dihydrogenphosphate, dipotassium hydrogenphosphate or magnesium phosphate; magnesium sulfate, sodium chloride and the like, for instance.

As the vitamins, there may be used vitamin B1, vitamin B12, vitamin C, and the like.

As the other organic nutrient sources, there may be used amino acids such as glycine, alanine, serine, threonine and proline. However, from a viewpoint of controlling the production cost, it is preferable to use only a minimum amount of organic nitrogen sources of peptone, meat extract and yeast extract, vitamins of vitamin B1, vitamin B12 and vitamin C, and organic nutrient sources of glycine, alanine, serine, threonine and proline. Particularly among them, the amount to be used of peptone, yeast extract and meat extract is more preferable to be kept in a minimum amount.

Not as long as P(3HB-co-3HH), it is generally said that, in producing a polyester by a microorganism, the polyester is preferably accumulated within cells when a concentration of nutrients essential for growing such as nitrogen, phosphorus, and the like becomes low and an excess amount of carbon source exist in a medium. However, it has never been investigated in detail for what kinds of nutrient restrictions are preferable.

The present inventors have found that the productivity of P(3HB-co-3HH) becomes low in the case that nitrogen is restricted as compared with the case that phosphorus is restricted, and bacteriolysis is caused under the restriction of nitrogen although it depends on culture conditions. Therefore, in the method for producing the copolyester according to the present invention, phosphorus-restriction culture is adopted without restricting nitrogen.

In the present invention, the method of restricting phosphorus during the culture is not particularly restricted, and the conventional phosphorus-restriction culture conditions may be adopted. Moreover, needless to say, "restriction of phosphorus" in the present invention does not mean a condition that completely no phosphorus atom is contained in a medium but means a condition in which phosphorus as a nutrient source is contained in a minimum amount necessary for growing. That is, it means a condition with a growing amount of cells being defined by phosphorus, and does not exclude phosphorus contained in a small amount as an inorganic salt in a medium.

Generally, the oil or fat to be used for a fermentation by the microorganism may include natural oils which are supplied in a relatively stable manner such as soybean oil, corn oil, cottonseed oil, palm oil, palm kernel oil, coconut oil, peanut oil and rapeseed oil, respective fractions obtained by fractioning these oils, for example, fractional oils called in an oils and fats industry by the names of "palm W olein oil" (low-melting point fraction obtained by fractionating palm oil twice without solvent), "palm kernel olein oil" (low-melting point fraction obtained by fractionating palm kernel oil once without solvent) or the like, and further a mixed oil obtained by mixing these oils. However, in the production method of the present invention, it is preferable to use an oil or fat containing lauric acid in constituent fatty acids, for example, an oil called as "lauric oils" in the oils and fats industry.

As the oil or fat containing lauric acid in constituent fatty acids may include, for example, natural oils such as palm kernel oil and coconut oil, and respective fractions obtained by fractionating these oils, for example fractional oils such as palm kernel olein oil, and it is preferable to use a natural or fractionated lauric oils. Additionally, there is no problem to use an oil or fat in which lauric acid is introduced in constituent fatty acids by treating an oil or fat containing no lauric acid chemically or biochemically, or the one in which the content of lauric acid is increased by treating a natural lauric oil biochemically. Furthermore, there may be used a mixed oil obtained by mixing 2 or more species of oils and fats containing lauric acid in constituent fatty acids, or a mixed oil obtained by mixing an oil or fat containing lauric acid in constituent fatty acids and an oil or fat containing no lauric acid in constituent fatty acids.

As the above carbon source, saccharides such as glucose, fructose, sucrose and lactose may be used together with an oil or fat containing lauric acid in constituent fatty acid in the production of the copolyester according to the present invention.

As the content of lauric acid in constituent fatty acids of the oil and fat to be used in the present invention (in the case that a mixed oil is used, it is calculated as a total content in constituent fatty acids of the mixed oil) is preferably not less than 10% by weight, and more preferably not less than 20% by weight. It is preferable to make the lauric acid content in constituent fatty acids of the oil and fat be not less than 10% by weight for securing the productivity of not less than 40 g/L and for producing a copolyester having not less than 4 mol % of the 3HH content.

As an addition mode of the oil and fat, any modes such as a shot of a large amount at once, addition in portions and continuous(stepwise) feed may be applied in the present invention. However, as a result of the investigation conducted by the present inventors, it was found that when a large amount is shot at once, toxicity for cells may appear by the oil or fat, which is water-insoluble components in a medium, or by fatty acids generated by hydrolysis of the oil or fat by lipase, or an actual operation may become difficult owing to foaming attributed to the fatty acids generated. Therefore, the oil or fat as a carbon source is preferably added in portions little by little, or fed continuously or intermittently by using a pump and the like.

According to the current technologies, it is difficult to accurately measure an amount of an oil or fat of water-insoluble components in a medium, or fatty acids generated by hydrolysis of an oil or fat by lipase either on-line or off-line. Thereupon, the present inventors have obtained a feed pattern, in which supply of an oil or fat is not insufficient but is not excess as causing a foaming, empirically from many experiments using a jar fermentor and developed a method adopting this pattern as a basic guideline. In an actual operation, it is preferable to apply a method comprising supplying the oil or fat with feeding along this guideline, sampling at every certain period, centrifuging, and adjusting the feeding amount with observing the thickness of an oil or fat layer in the culture supernatant.

As a result of the investigation conducted by the present inventors, it was confirmed that the guideline thus produced may also be applied efficiently in a culture using a large fermentor.

As another indirect method, there maybe mentioned a method comprising measuring an oxygen concentration and a carbon dioxide concentration in an exhaust gas to obtain an oxygen consuming rate or a carbon dioxide generation rate. Using these values as an index, a feed rate of the oil or fat may be changed. In this case, it is preferable to study a respiration property of cell growing period and polyester production period in detail beforehand and make an adjustment.

In the production method according to the present invention, the range of the 3HH content of the produced copolyester may be controlled optionally due to a species of the oil or fat to be added as a carbon source. For example, in the cases that the lauric oils such as coconut oil, palm kernel oil or a fractional oil or fat of said oils and fats are used alone or in admixture as the carbon source, P(3HB-co-3HH) having relatively high 3HH content of 4 to 20 mol % may be obtained. In the cases that mixed oils containing soybean oil, corn oil, cottonseed oil, palm oil, peanut oil, rapeseed oil or a fractional oil of these oils, which contain no lauric acid in constituent fatty acids, and the above lauric oils are used, P(3HB-co-3HH) having relatively low 3HH content of not more than 10 mol % may be produced.

Moreover, by adjusting the mixing ratio of said mixed oils to change the lauric acid content in constituent fatty acids, multiple species of P (3HB-co-3HH) having an optional 3HH content may be produced while maintaining the high productivity of not less than 40 g/L. Furthermore, to produce a copolymer having a third component other than 3HB and 3HH, a carbon source corresponding to the third component, for example a fatty acid having odd number of carbon chains may be added to the oil and fat containing lauric acid in the above constituent fatty acids.

The culture temperature of the microorganism may be any temperatures as long as the cells may grow, but preferably at 20 to 40° C., more preferably at 25 to 35° C. The culture period is not particularly restricted and may be 1 to 7 days, preferably 40 to 70 hours.

The above explained restriction of the species of the oil or fat, restriction of phosphorus or the like in producing the polyester is carried out in a main culture in a polyester production medium. Incidentally, the microorganisms are generally cultured in a seed medium or a preculture medium to grow cells to a certain level prior to the main culture with the polyester production medium. In such a case, the same nutrient sources as described above maybe used in the seed medium or the preculture medium. The culture temperature in these media may be the same as the above polyester production medium, and the culture period is preferably 1 to 2 days, respectively.

Additionally, when the transformed microorganism is used as a microorganism, for example, antibiotics such as kanamycin, ampicillin and tetracycline, which correspond to a resistant gene exist in vectors and the like, may be added to a preculture medium.

In the production method of the present invention, a method for collecting the copolyester from the microorganism is not particularly restricted, and the conventional solvent extraction methods, physical cell disruption, and chemical treatment, etc. may be used and the following methods may also be used, for instance. After completion of a culture, cells are separated from a culture broth by a centrifuge and the like, then the cells are washed with distilled water, methanol and the like, and dried. A polyester is extracted from the dried cells using organic solvents such as chloroform. Cell components are removed from the polyester-containing organic solvent by filtration, etc., and poor solvents such as methanol and hexane are added to the filtrate and precipitate the polyester. The supernatant is removed by filtration or centrifugation, and dried to collect a polyester.

The monomeric unit of the polyester obtained can be analyzed by gas chromatography or nuclear magnetic resonance spectrometry, for instance.

BEST MODE FOR CARRYING OUT THE INVENTION

Figure 1:
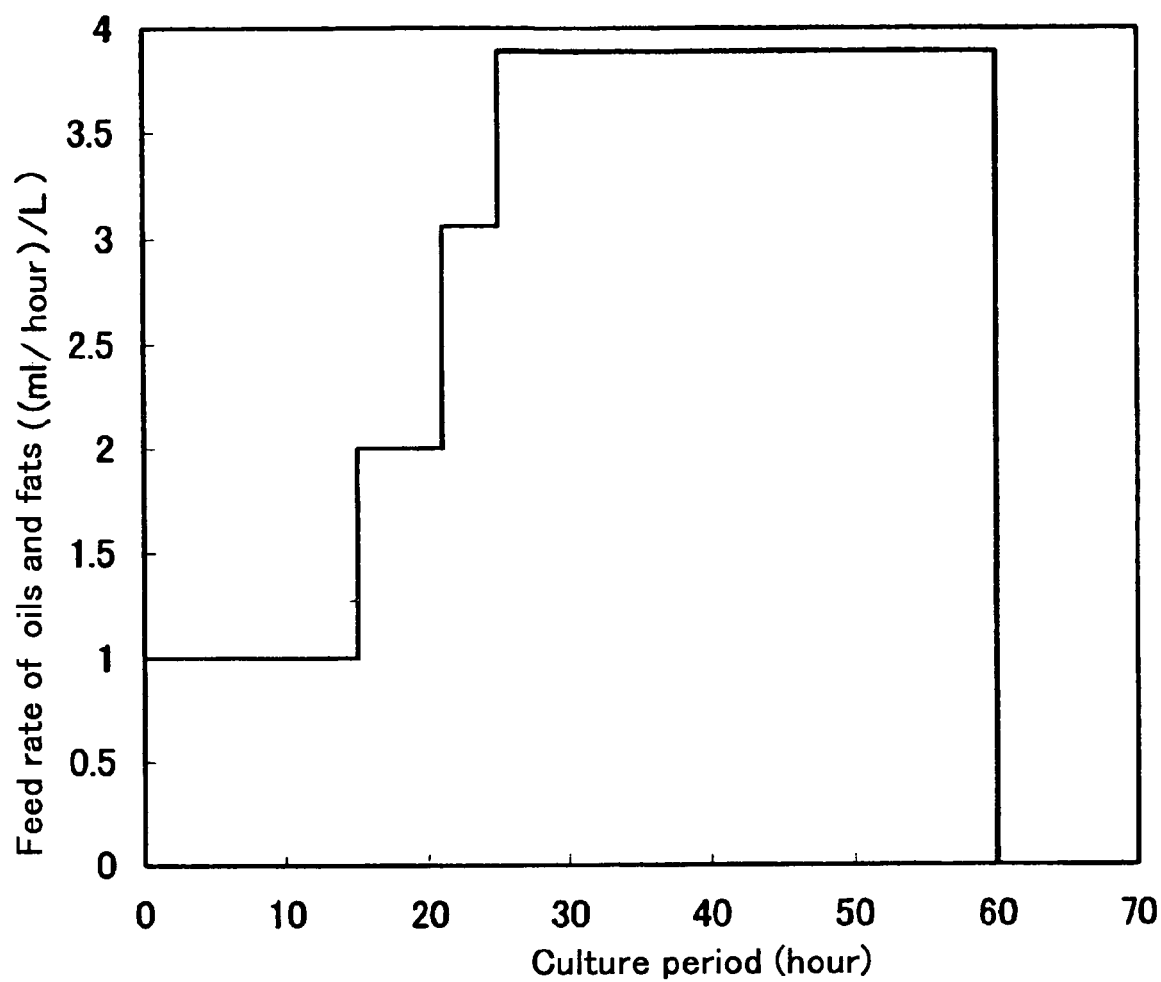
FIG. 1 is a guideline showing a feed pattern in Example 1, 4, 5 and Comparative Example 1.

The following examples illustrate the present invention more specifically. These examples are, however, by no means limitative of the technical scope of the present invention.

EXAMPLE 1 AND COMPARATIVE EXAMPLE 1

Ralstonia eutropha strain PHB-4/pJRDEE32d13 (T. Fukui., Y. Doi., Appl. Microbiol. Biotechnol., 49, 333–336 (1998)) (hereinafter, referred to briefly as "Red 13" strain) was cultured as follows. Incidentally, as described above, said Red 13 strain is deposited to the National Institute of Advanced Industrial Science and Technology, International Patent Organism Depositary (Central 6, 1-1-1, Higashi, Tsukuba, Ibaraki, JAPAN)on the date of Aug. 7, 1997 under the name of *Alcaligenes eutrophus* AC 32 in an accession number of FERM BP-6038 under Budapest treaty.

The composition of the seed medium was made to comprise 1 w/v % Meat-extract, 1 w/v % Bacto-Trypton, 0.2 w/v % Yeast-extract, 0.9 w/v % $Na_2PO_4 \square 12H_2O$, 0.15 w/v % $KH_2PO_4$ and pH 6.8.

The composition of the preculture medium was made to comprise 1.1 w/v % $Na_2PO_4 \square 12H_2O$, 0.19 w/v % $KH_2PO_4$, 1.29 w/v % $(NH_4)_2SO_4$, 0.1 w/v % $MgSO_4 \square 7H_2O$, 2.5 w/v % palm W olein oil, 0.5 v/v % trace metal salt solution (1.6w/v % $FeCl_3 \square 6H_2O$, 1 w/v % $CaCl_2 \square 2H_2O$, 0.02 w/v % $CoCl_2 \square 6H_2O$, 0.016 w/v % $CUSO_4 \square 5H_2O$ and 0.012 w/v % $NiCl_2 \square 6H_2O$ were dissolved in 0.1 N hydrochloric acid), and $5 \times 10^{-6}$ w/v % kanamycin.

The composition of the polyester production medium was made to comprise 0.385 w/v % $Na_2PO_4 \square 12H_2O$, 0.067 w/v % $KH_2PO_4$, 0.291 w/v % $(NH_4)_2SO_4$, 0.1 w/v % $MgSO_4 \square 7H_2O$, 0.5 v/v % trace metal salt solution (1.6 w/v % $FeCl_3 \square 6H_2O$, 1 w/v % $CaCl_2 \square 2H_2O$, 0.02 w/v % $CoCl_2 \square 6H_2O$, 0.016 w/v % $CuSO_4 \square 5H_2O$ and 0.012 w/v % $NiCl_2 \square 6H_2O$ were dissolved in 0.1 N hydrochloric acid) and 0.05 w/v % BIOSPUREX 200K (antifoaming agent: product of Cognis Japan Ltd.)

A glycerol stock (50 µl) of Red 13 strain was inoculated to a seed medium (10 ml) and cultured for 24 hours. Then, the resultant was inoculated in a ratio of 0.2 v/v % to a 5 L jar fermentor (MDL-500 type, product of B.E. Marubishi Co., Ltd.) containing 3 L of the preculture medium. The running condition was set to be a culturing temperature of 30° C., a stirring rate of 500 rpm, an aeration rate of 1.8 L/min. The culture was carried out for 28 hours with controlling pH between 6.7 and 6.8 to obtain a culture seed. 7% ammonium hydroxide solution was used for the pH control.

The polyester production culture was carried out as the following. Nine of 10 L jar fermentors (MDL-1000 type, product of B.E. Marubishi Co., LTD) containing 6 L of the production medium were made ready, and 1.0 v/v % of the preculture seed was inoculated to the respective media. Then, 9 species of oils and fats, that is, soybean oil, cottonseed oil, rapeseed oil, corn oil, palm W olein oil, peanut oil, coconut oil, palm kernel oil and palm kernel olein oil were added to the respective jar fermentors. These oils and fats were added to an initial medium at a ratio of 1 w/v %, and fed as following the guideline shown in FIG. 1 (a feed pattern in which supply of the oil or fat is not insufficient but is not excess). Incidentally, the unit "(ml/hour)/L" of feed rate of the oil or fat in FIG. 1 represents a feed rate (ml) of the oil or fat per 1 L of the culture broth by hour. The running condition was set to be a culturing temperature of 28° C., a stirring rate of 400 rpm, an aeration rate of 3.6 L/min and pH was controlled of between 6.7 and 6.8. The culture was carried out for 60 hours, and after completion of the culture, cells were collected by a centrifugation, washed with methanol and lyophilized to measure the weight of the dried cells.

To approximately 1 g of the dried cell obtained was added with 100 ml of chloroform, and the mixture was stirred overnight at a room temperature to extract a polyester within cells. After the cell residue was filtered off, the resultant was concentrated by an evaporator until the total content to be 30 ml, approximately 90 ml of hexane was added gradually with stirring slowly, and allowed to stand for 1 hour. The precipitated polyester was filtered off, and dried in vacuo for 3 hours at 50° C. The weight of the dried polyester was measured and the content of the polyester within the cells were calculated.

Approximately 20 mg of the obtained dried polyester was added with 2 ml of a sulfuric acid-methanol mixture (15:85) and 2 ml of chloroform, and the container was sealed. The obtained mixture was heated at 100° c. for 140 minutes to obtain methylester of a polyester decomposition product. After cooling, 1.5 g of sodium bicarbonate was added by little and little to neutralize, and the mixture was left until generation of carbon dioxide stops. After 4 ml of diisopropyl ether was added and well-mixed, the mixture was centrifuged to analyze a composition of hydroxyalkanoic acid methyl ester of the polyester decomposition product in a supernatant by a capillary gas chromatography, and a composition (content) of a monomer unit of the obtained polyester was determined. The used gas chromatograph was GC-17A produced by Shimadzu Corporation, and the used capillary column was NEUTRA BOND-1 produced by GL Science Co., LTD (column length 25 m, column inner diameter 0.25 mm and liquid film thickness 0.4 μm). The temperature raising rate was set to be 8° c./min from 100° c. of an initial temperature to 200° c., and further 30° c./min from 200° c. to 290° c.

The effects given by differences of lauric acid content in respective oils and fats and species of the oils and fats used as carbon sources on a 3HH mole fraction ratio of P(3HB-co-3HH) and the productivity were shown in Table 1. Table 1 shows the results of the culture at 60-hour.

TABLE 1

| | Oils and fats | Productivity of P(3HB-co-3HH) (g/L) | 3HH content (mol %) | Lauric acid content in the used oil (weight %) |
|---|---|---|---|---|
| Comparative Example 1 | Soybean oil | 62 | 3.0 | 0 |
| | Cottonseed oil | 56 | 2.5 | 0 |
| | Rapeseed oil | 52 | 2.7 | 0 |
| | Corn oil | 68 | 2.7 | 0 |
| | Palm W olein oil | 62 | 3.0 | 0 |
| | Peanut oil | 45 | 3.6 | 0 |
| Example 1 | Coconut oil | 42 | 13.8 | 47 |
| | Palm kernel oil | 48 | 6.8 | 47 |
| | Palm kernel olein oil | 71 | 7.9 | 41 |

From the results, it was found that when coconut oil, palm kernel oil or palm kernel olein oil, which contain lauric acid in constituent fatty acids, were used, the 3HH contents of the polyester obtained were as high as about 7 to 14 mol %, and the 3HH contents of all the other fats containing no lauric acid in constituent fatty acids were lower than 4 mol %. It was found that the 3HH contents, which has a remarkable effect on qualities and characteristics of the polyester, differ significantly depending on the difference of the oil or fat used as a substrate and presence or absence of lauric acid. Although the lauric oils other than palm kernel olein oil were slightly low in the productivity of the polyester compared with the other oils and fats, the productivity capable of being applied for an industrial production, that is not less than 40 g/L, was secured.

EXAMPLE 2 AND COMPARATIVE EXAMPLE 2

Using the same oil as of Example 1 and Comparative Example 1, the strain was cultured in the same manner as in Example 1 and Comparative Example 1 except that the respective oils and fats are added in a ratio of 3 w/v (%) into an initial medium and in a ratio of 2 w/v (%) at every 12 hours up to 48 hours. The results of the culture at 60-hour are shown in Table 2.

TABLE 2

| | Oils and fats | Productivity of P(3HB-co-3HH) (g/L) | 3HH content (mol %) |
|---|---|---|---|
| Comparative Example 2 | Soybean oil | 64 | 2.5 |
| | Cottonseed oil | 60 | 2.3 |
| | Rapeseed oil | 56 | 2.1 |
| | Corn oil | 71 | 2.2 |
| | Palm W olein oil | 65 | 2.8 |
| | Peanut oil | 45 | 3.8 |
| Example 2 | Coconut oil | 45 | 10.4 |
| | Palm kernel oil | 48 | 5.9 |
| | Palm kernel olein oil | 72 | 5.8 |

Foams were generated more vigorously than Example 1 and Comparative Example 1 throughout the cultures in any oils and fats. However, the high productivity of not less than 40 g/L and the desired 3HH content of not less than 4 mol % were obtained when coconut oil, palm kernel oil or palm kernel olein oil was used, which contains a large amount of lauric acid, also in the cases where the oils and fats were added in portions.

EXAMPLE 3 AND COMPARATIVE EXAMPLE 3

Using the same oil as of Example 1 and Comparative Example 1, the strain was cultured in the same manner as in Example 1 and Comparative Example 1 except that the respective oils and fats were fed at a constant feed rate of 15 ml/h from 0 to 57-hour. The results of the culture at 60-hour are compared in Table 3.

TABLE 3

| | Oils and fats | Productivity of P(3HB-co-3HH) (g/L) | 3HH content (mol %) |
|---|---|---|---|
| Comparative Example 3 | Soybean oil | 60 | 2.7 |
| | Cottonseed oil | 54 | 2.7 |
| | Rapeseed oil | 50 | 2.5 |
| | Corn oil | 66 | 2.3 |
| | Palm W olein oil | 64 | 2.7 |
| | Peanut oil | 42 | 3.9 |
| Example 3 | Coconut oil | 43 | 9.6 |
| | Palm kernel oil | 45 | 5.6 |
| | Palm kernel olein oil | 70 | 6.0 |

Foams were generated more vigorously than Example 1 and Comparative Example 1 in the middle stage of the culture in any oils and fats. However, the high productivity of not less than 40 g/L was obtained when coconut oil, palm kernel oil and palm kernel olein oil were used, which contain large amount of lauric acid, also in the cases where the oils and fats were fed at a constant rate while securing the 3HH content of not less than 4 mol %.

EXAMPLE 4

The strain was cultured in the same medium and condition as in Example 1 and Comparative Example 1 except that mixed oils were used, which comprise palm kernel olein oil and coconut oil in 1:1 (v/v), palm kernel olein oil and peanut oil in 1:1 (v/v), palm kernel olein oil and soybean oil in 1:1 (v/v) and palm kernel olein oil and corn oil in 1:1 (v/v), and the results shown in Table 4 were obtained. The results of the culture at 60-hour are compared in Table 4.

TABLE 4

| Mixed oils | | Productivity of P(3HB-co-3HH) (g/L) | 3HH content (mol %) |
|---|---|---|---|
| Palm kernel olein oil and coconut oil | 1:1 (v/v) | 68 | 8.5 |
| Palm kernel olein oil and peanut oil | 1:1 (v/v) | 65 | 6.2 |
| Palm kernel olein oil and soybean oil | 1:1 (v/v) | 72 | 5.2 |
| Palm kernel olein oil and corn oil | 1:1 (v/v) | 67 | 4.5 |

As a result of increasing the lauric acid content in substrate oils and fats by using the mixed oils containing a lauric oil, P(3HB-co-3HH) having the 3HH content of not less than 4 mol % were produced even when corn oil and soybean oil were used, which produced P (3HB-co-3HH) having the 3HH content of not more than 3 mol % in Comparative Example 1.

In the case of peanut oil and coconut oil, by using the oils in the forms of mixed oils, the productivities were improved, and the 3HH content showed a medium value of the respective oils and fats before mixing.

EXAMPLE 5

The strain was cultured in the same medium and condition as in Example 1 and Comparative Example 1 except that 4 species of mixed oils in which the mixing ratio of palm kernel olein oil and soybean oil was changed were used as a substrate, that is, mixed oil A (palm kernel olein oil/soybean oil=75/25 (v/v)), mixed oil B (palm kernel olein oil/soybean oil=50/50(v/v)), mixed oil C (palm kernel olein oil/soybean oil=25/75 (v/v)) and mixed oil D (palm kernel olein oil/soybean oil=20/80 (v/v)). The results shown in Table 5 were obtained. The results of the culture at 60-hour are compared in Table 5.

TABLE 5

| Mixed Oils | Productivity of P(3HB-co-3HH) (g/L) | 3HH content (mol %) | Lauric acid content in the used oil (weight %) |
|---|---|---|---|
| Mixed oil A (Palm kernel olein oil/Soy bean oil = 75/25 (v/v)) | 68 | 6.1 | 30.8 |
| Mixed oil B (Palm kernel olein oil/Soybean oil = 50/50 (v/v)) | 72 | 5.2 | 20.5 |
| Mixed oil C (Palm kernel olein oil/Soybean oil = 25/75 (v/v)) | 70 | 4.7 | 10.3 |
| Mixed oil D (Palm kernel olein oil/Soybean oil = 20/80 (v/v)) | 72 | 3.2 | 8.2 |

As shown in Table 5, differences were not significantly acknowledged in the productivity depending on differences of the mixing ratio. However, the 3HH content became high as the ratio of palm kernel olein oil in the mixed oils was large. Particularly, the mixed oils containing not less than 10% by weight of lauric acid could produce P(3HB-co-3HH) having the desired 3HH content of not less than 4 mol % and expressing preferable characteristics.

INDUSTRIAL APPLICABILITY

In the method according to the present invention, P(3HB-co-3HH) having the desired 3HH content and expressing preferable characteristics may be produced while securing the high productivity of not less than 40 g/L by restricting phosphorus and using oils or fats containing lauric acid as a carbon source. Moreover, by making the content of lauric acid in constituent fatty acids in the oils or fats to be not less than 10% by weight, P(3HB-co-3HH) having the 3HH content of not less than 4 mol % may be produced while securing the high productivity of not less than 40 g/L. Accordingly, it becomes possible to produce or provide P(3HB-co-3HH) having a broad application range in the industrial field.

The invention claimed is:

1. A method for producing a copolyester comprising at least 3-hydroxybutyric acid and hydroxyhexanoic acid as monomeric units by a microorganism
which comprises culturing the microorganism with an oil or fat containing lauric acid in constituent fatty acids as a carbon source under condition phosphorus, a nutrient source, being restricted,
wherein the lauric acid content in constituent fatty acids of the oil or fat is 10 to 41% by weight.

2. The method according to claim 1,
wherein the oil or fat containing lauric acid is palm kernel olein oil.

3. The method according to claim 1,
wherein the oil and fat used as a carbon source is a mixed oil obtained by mixing palm kernel olein oil and an oil or fat containing no lauric acid in constituent fatty acids.

4. The method according to claim 3,
wherein the oil or fat containing lauric acid is a mixed oil obtained by mixing palm kernel olein oil and at least one oil or fat selected from the group consisting of peanut oil, soybean oil and corn oil.

5. The method according to claim 1,
wherein the microorganism is a transformed microorganism incorporated with a polyester polymerase gene isolated from *Aeromonas caviae*.

6. The method according to claim 1,
wherein the microorganism is *Ralstonia eutropha*.

* * * * *